United States Patent
Rubin

(10) Patent No.: US 11,260,093 B2
(45) Date of Patent: *Mar. 1, 2022

(54) ENHANCED MYCELIUM GROWTH MEDIUM AND METHOD

(71) Applicant: Ancient Brands, LLC, Franklin, TN (US)

(72) Inventor: Jordan Seth Rubin, College Grove, TN (US)

(73) Assignee: Ancient Brands, LLC, Franklin, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/802,185

(22) Filed: Feb. 26, 2020

(65) Prior Publication Data

US 2020/0187432 A1  Jun. 18, 2020

Related U.S. Application Data

(62) Division of application No. 15/443,146, filed on Feb. 27, 2017, now Pat. No. 10,609,873.

(60) Provisional application No. 62/300,324, filed on Feb. 26, 2016.

(51) Int. Cl.
| | |
|---|---|
| *A61K 36/062* | (2006.01) |
| *A61K 36/074* | (2006.01) |
| *A61K 36/07* | (2006.01) |
| *A23L 33/105* | (2016.01) |
| *C05F 11/00* | (2006.01) |
| *A01G 22/22* | (2018.01) |
| *A01G 18/50* | (2018.01) |
| *A01G 7/04* | (2006.01) |

(52) U.S. Cl.
CPC ............ *A61K 36/062* (2013.01); *A01G 7/045* (2013.01); *A01G 18/50* (2018.02); *A01G 22/22* (2018.02); *A23L 33/105* (2016.08); *A61K 36/07* (2013.01); *A61K 36/074* (2013.01); *C05F 11/00* (2013.01); *A23V 2002/00* (2013.01); *A61K 2236/11* (2013.01)

(58) Field of Classification Search
CPC ........ A01G 18/00; A01G 7/045; A01G 22/22; A01G 1/04; A01G 16/00; A01G 18/20; A61K 36/062; A61K 36/074; A61K 36/07; A61K 2236/11; A23L 33/105; A23V 2002/00; A01H 1/044; A01H 7/04; C12N 1/14; C05F 11/00; C05F 11/02
See application file for complete search history.

(56) References Cited

U.S. PATENT DOCUMENTS

| 7,178,285 B2 | 2/2007 | Miller et al. |
| 10,609,873 B2 * | 4/2020 | Rubin .................. A23L 33/105 |
| 2015/0305219 P1 | 10/2015 | Miller et al. |

OTHER PUBLICATIONS

Jiang et al., "Novel Medicinal Mushroom Blend . . . " Int. J. Oncol., 37(6): 1529-36 (2010).

* cited by examiner

*Primary Examiner* — Kent L Bell
(74) *Attorney, Agent, or Firm* — Barbara E. Johnson

(57) ABSTRACT

The invention is a method for enhanced growth of mycelium in culture including the key steps of seed blend choice from among corn, rice, quinoa, chia, canihua, cumin and flax seed, germinating the seed blend prior to inoculating the mycelium starter, and conducting the mushroom cultivation with water and particular transmissions of sound and particularly colored light. Mushrooms grown by such a method not only mature in 13-15 days rather than 21 days, but have an enhanced nutritional and medicinal profile along with absence of unwanted organism contaminants whose unwanted overgrowth occurs during days 16-21 (or days 16-28) of typical mushroom culture.

9 Claims, No Drawings

ENHANCED MYCELIUM GROWTH MEDIUM AND METHOD

FIELD OF THE INVENTION

The invention pertains to substrates and methods for mushroom growth which yield new and surprisingly improved results in mushroom growth speed as well as nutritional and medicinal profile.

BACKGROUND OF THE INVENTION

Description of Related Art

The quiet yet spectacular growth of the medicinal and nutritive mushroom industry is something that (at this writing) has not come to the attention of the average educated reader in the United States. Nutritional supplementation still tends to connote vitamins and minerals, perhaps administered in combination form in pills or capsules, or various "herb du jour" trends in which Ginkgo biloba may be popular one day, and Garcinia cambogia the next. Omega 3 fatty acids, alpha lipoic acid, glucosamine, vitamin $K_2$ and other nutritional supplements are widely regarded and widely consumed—and available everywhere including the corner drug store. Alternative health and medicinal interventions are more and more beloved by Americans every year. Even so, when an average American thinks Health Care, he or she does not yet immediately think, "Mushrooms."

However, such attitudes are changing—and for good reason. The idea of the "medicinal mushroom" is not marketing hype. No less than the *International Journal of Oncology* published, in 2010, how medicinal mushrooms have shown promise in the fight against cancer by suppressing growth and invasiveness of human breast cancer cells. In fact, it is instructive to view the journal citation and abstract in its original form, as follows, and while bearing in mind that there are countless similar journal articles in publication of which the following is simply one example: Jiang Jl, Sliva D., "Novel medicinal mushroom blend suppresses growth and invasiveness of human breast cancer cells," *Int J Oncol.* 2010 December; 37(6):1529-36 (abstract) Mushrooms are an integral part of Traditional Chinese Medicine (TCM), and have been used for millennia to prevent or treat a variety of diseases. Currently mushrooms or their extracts are used globally in the form of dietary supplements. In the present study we have evaluated the anticancer effects of the dietary supplement, MycoPhyto® Complex (MC), a novel medicinal mushroom blend which consists of a blend of mushroom mycelia from the species *Agaricus blazei, Cordyceps sinensis, Coriolus versicolor, Ganoderma lucidum, Grifola frondosa* and *Polyporus umbellatus*, and β-1,3-glucan isolated from the yeast, *Saccharomyces cerevisiae.* Here, we show that MC demonstrates cytostatic effects through the inhibition of cell proliferation and cell cycle arrest at the G2/M phase of highly invasive human breast cancer cells MDA-MB-231. DNA-microarray analysis revealed that MC inhibits expression of cell cycle regulatory genes (ANAPC2, ANAPC2, BIRC5, Cyclin B1, Cyclin H, CDC20, CDK2, CKS1B, Cullin 1, E2F1, KPNA2, PKMYT1 and TFDP1). Moreover, MC also suppresses the metastatic behavior of MDA-MB-231 by the inhibition of cell adhesion, cell migration and cell invasion. The potency of MC to inhibit invasiveness of breast cancer cells is linked to the suppression of secretion of the urokinase plasminogen activator (uPA) from MDA-MB-231 cells. In conclusion, the MC dietary supplement could have potential therapeutic value in the treatment of invasive human breast cancer.

This is not to say that the health benefits of mushrooms have gone completely unnoticed in the general population to date. Currently, international retailer GNC sells a Mushroom Complex nutritional supplement which contains powders and/or extracts of Maitake, Reishi and Shiitake mushrooms. U.S. Pat. No. 6,805,866 discloses a combination of blended mushrooms in an oral supplement composition that, upon administration, provides a method of enhancing the immune system. Furthermore, medicinal and nutritive mushrooms have not only their own intrinsic chemistry and concomitant beneficial properties, they are also particularly well suited to taking up beneficial nutrients from the substrates on which they are grown. U.S. Pat. No. 7,178,285 discloses a method of growing high anthocyanin content mushrooms on high anthocyanin substrates such as purple corn, black corn, purple rice, and so on. United States Published Patent Application No. 20150305249 takes this beneficial-media concept to the next level and discloses that the medium should not only contain one or more high anthocyanin grains, those grains should be sprouted or germinated prior to inoculation of the mycelium for cultivation. These solid technology advances have contributed substantially to commercial nutritive and medicinal mushroom cultivation in the United States. A need remains, however, for an optimized mushroom growing protocol that maximizes the desired nutritional profile and significantly speeds mushroom growth, to enhance not only the quality and constitution of the end product but also the absence of overgrowth of unwanted organisms due to the improved cultivation speed and integrity.

SUMMARY OF THE INVENTION

In order to meet this need, the present invention is a four pronged mycelium culture method in which the (a) choice of seeds for the substrate, (b) the sprouting of the seeds prior to mycelium inoculation, and (c) the combination of hydration with a specific type of water with (d) exposure to a particular spectrum of light/color/sound yield new and unexpectedly improved results in speed of mushroom growth and optimized nutritional and medicinal profile. Mushrooms grown with the present method complete their growth phase in 13-15 days rather than the expected 21-28 day growth cycle typical of prior art mushroom culture. The much faster growth, compared to prior art mushroom culture, is a benefit in itself for practical and commercial reasons, but the speed of cultivation reduces or eliminates overgrowth in the medium of undesirable organisms which, in turn, enhances the purity of the end product prepared in addition to its constitutive profile.

DETAILED DESCRIPTION OF THE INVENTION

Because the present invention includes the four elements of choice of seed blend, germinating the seeds, inoculating the mycelium onto the seed blend substrate and cultivating the growing mushrooms in the presence of a particular type of water together with specific spectra of light/color and sound, the first order of business is to select and prepare the seed blend. The present mushroom growth substrate contains at least three, preferably five and most preferably eight seeds in combination. These seeds may be selected from the group consisting of corn (preferably purple corn), quinoa (preferably black or red quinoa or both), canihua (preferably red canihua), chia (preferably black chia), cumin (preferably black cumin), flax seed (preferably red flax seed) and rice (preferably black or purple rice). When both black and red quinoa are combined with all the other seeds listed (either black or purple rice), this yields an eight-seed blend. However, as few as three choices are possible within the scope of the invention, such as chia plus flax seed plus canihua. After the choices leading to the desired seed blend are made, the seed blend is sprouted according to seed sprouting techniques well known in the art. Germination should proceed for 18-48 hours before mycelium inoculation takes place.

While the use of colored seeds generally in mushroom growth medium is already known, from U.S. Pat. No. 7,178,285, the particular blend including all of corn, quinoa, canihua, chia, cumin, flaxseed and rice (preferably in their colored versions as described above) provides a distinct nutritional profile as well as growth dynamic that using only one or two of these seeds cannot provide alone. Quinoa, apart from its stature as a grain which provides a complete protein to humans, is also high in the amino acid lysine, and also manganese, copper, zinc and iron. Canihua also provides complete proteins to humans and is a rich source of iron, magnesium and calcium. Chia seeds also contain all amino acids essential to humans and are high in omega 3 and omega 6 fatty acids, caffeic acid, chlorogenic acid, kaempferol, myricetin, quercetin, calcium, iron, magnesium, phosphorus, potassium and zinc. Cumin seeds are rich in iron, copper, calcium, potassium, manganese, selenium, zinc and magnesium. Flax seeds are high in omega 3, omega 6 and omega 9 fatty acids. Rice is high in thiamine, niacin and Vitamin K. Corn is high in Vitamin C, thiamine, niacin, riboflavin, panthothenic acid, pyridoxine, folate and choline. The colorful versions of these seeds are all high in anthocyanins, as well as the above-listed nutrients. Sprouting these seed mixtures before adding the mycelium inoculant does not just take seemingly hard, impervious encapsulated seeds and turn them into softer, accessible sprouts, although that is indeed part of the advantage of sprouting in the mushroom growth context. Germination also biochemically removes barriers to bioavailability of the desirable seed constituents, such as the undesirable phytic acid or other antinutrients such as enzyme inhibitors, by hydrolyzing them as part of the sprouting phenomenon. Germinating the seeds or grains that make up the mushroom growth medium was disclosed in U.S. Published Patent Application No. 20150305249, and yet even that excellent method is still susceptible of further improvement. It turns out that the present invention improves on the germination taught by U.S. Published Patent Application No. 20150305249 not only by using particularly powerful seed blends (see below), but also method enhancements integral to the use of the structured water and color/light and sound protocols discussed later in this patent specification. Germination of the seed blends of this invention take place by moistening the seeds in the seed blend with structured "energized" water described below, and allowing a germination period of between 18 and 48 hours, preferably 36 hours, prior to inoculation with the mycelium culture.

The above-described seed blends were determined by trial and error experimentation, with as few as three of the seeds' (chia, flax seed and canihua) giving improved results up to the preferred embodiment of the invention, all eight seeds', giving the greatest enhancement of already-improved yields available possibly with only three seeds. Upon review of the results of the trial and error selection, however, it is apparent to the inventor what part of the source of the substrate strength is: the incorporation of at least two complete protein seeds (complete protein's meaning all the essential amino acids for human consumption) combined with at least one structural seed gives the new and unexpectedly improved yield and purity results of the present invention. By "structural seed" is meant a seed with a relatively high cellulose content compared to all seeds generally such as the cereal grains corn or rice or the notably high fiber flax seed. By including high cellulose corn, rice or flax seed (or all three) in the seed blend of the present invention, together with at least two complete protein seeds, a synergy occurs wherein the high protein substrate foments fastest and healthiest possible mushroom culture while the high cellulose grain provides structural integrity to the growth medium. Without the high cellulose grain constituent in the growth medium, the softer whole protein grains such as canihua and chia would tend to collapse in on themselves during sprouting, under the weight of the mycelial growth. For this structural reason, the corn, rice or flax seed component of the present seed blend will generally be at least 50% of the seed blend, more preferably at least 65% of the seed blend and ideally greater than 90% of the seed blend, with the one or more seeds other than corn, rice and flax seed making up the balance of the blend but always with at least three of the seed types' being present. The combination of at least one cellulosic seed (corn, rice or flax seed) together with a minimum of two high protein seeds (chosen from quinoa, canihua or chia) is the insight of the present invention at the heart of the selection of the seed blend.

In addition to the improvements in seed blend selection discussed above, the present improved yields and profiles are also possible in part by growing nutritive and medicinal mushrooms on the above-described sprouted seeds together with a particular type of water, for hydration of the medium during mushroom growth, and also with the providing of light of certain colors as well as certain sounds defined by their frequencies.

In particular, the present method uses "structured, energized water" with high pH, low total dissolved solids and increased capability of oxidative redux potential (ORP). Increased capability of ORP is achieved when oxidative redux potential of the water is enhanced, with negative ORP values' indicating the highest ORP capability. In the treatment of the water used to hydrate the present mushroom culture substrates, the starting ORP of +400 is converted to the much enhanced −400 to −600 ORP, preferably −600 ORP value, prior to use. The same water is used to moisten the seed blend prior to germination as is used throughout mushroom culture to hydrate and maintain the culture growth.

In addition to the structured, energized water used in the present method, the present mushroom culture is grown while being subject to particular presentations of sound, and light and color frequencies. At least one or more of particular sound frequencies are "played" to the growing mushrooms during most if not all of the mushroom cultivation period: 396 Hz, 417 Hz, 444 Hz, 528 Hz, 639 Hz, 741 Hz and 852 Hz. In the preferred embodiment of the invention, all of these seven sound frequencies are transmitted to the mushroom culture in succession, at a range between 30 and 100 decibels, more preferably 50-80 decibels during 80% or more of the mushroom culture time between mycelial inoculation and harvest. These frequencies may be played alone or as the tonal backbone of music transmissions which feature them. While these frequencies are already known to have resonant match or complement with various human tissues and brain waves and concomitant beneficial effects on both, these frequencies have not to the inventor's knowledge ever been used before to enhance mushroom culture. At the same time the sound frequencies are transmitted, the mushroom culture is also subjected to transmissions of visible light in the color ranges "throughout the rainbow" but without yellow, namely, purple, blue, green, orange and red and shades in between (but not yellow). Moreover, the light transmissions in these colors should be between 250-3000 lumens, more preferably 500-2000 lumens, for every 25,000 square feet (gross) of cultivation space, with the light/color transmission's being the only light in the room.

Except for the method steps explained in detail above, the mushroom culture described in this specification can be for any known edible, nutritive or medicinal mushroom species. Preferably, the mushrooms grown with the present method will be one or more of *Amanita muscaria* (Fly Agaric), *Armillaria mellea* (Honey Mushroom), *Auricularia auricula, Auricularia polytricha, Boletus edulis* (King Bolete), *Calvatia* species (Puffball), *Canterellus cibarius* (Chanterelle), *Clitocybe nuda* or *Tricholoma nudum* or *Lepista nuda* (Blewit), *Cordyceps ophioglossoides* (Club-head Fungus), *Cordyceps sinensis* (Caterpillar Fungus), *Fomes fiomentarius* (True Tinder Polypore, Amadou), *Formitopsis officinalis, Boletus officinais, Polyporus officinalis* (Quinine Conk, White agaric, agaric, purging agaric, larch agaric), *Fomitopsis pinicola* (Red Belted Polypore), *Ganoderma applanatum* (Artist's Conk), *Ganoderma lucidum* (Varnish Conk, Ling chih, Ling qi, Ling-Zhi, Reishi), *Geastrume triplex* (Earthstar), *Grifola frondosa* (Maitake, Hen of the Woods, Sheep's Head), *Grifola umbellate* (*Polyporus sclerotium*), *Heterobasidion annosum* (Birch polypore), *Inonotus obliquus, Poria obligua, Polyporus obliquus* (Chaga, Pilat, Clinker Polypore, Birch mushroom, Black Birch touchwood), *Fungus japonicus* (Kombucha), *Russula* and *Lacterius* species including *Lacterius deliciosus* (Saffron or Orange-latex Milky, *Lentinula edodes* (Shiitake), *Lenzites betulina* (Gilled Polypore, Kaigaratake), *Morchella esculenta* (Morel), *Peziza vesiculosa* (Bladder Cup), *Phallus impudicus* (Stinkhorn), *Phellinus ignarius, Fomes ignarius*, or *Polyporus ignarius* (False Tinder), *Piptoporus betulinus* (Birch Conk or Polypore), *Pleurotus ostreatus* (Oyster Mushroom, Hiratake), *Polyporus squamosus* (Dryad's Saddle), *Pycnoporus Sanguineus, Trametes cinnabarina* (Red Polypore), *Schizophyllum commune* (Split-Gill), *Suilus luteus* (Slippery Jack), or *Trametes versicolor* (Turkey Tail). However, this list of suitable culinary and medicinal mushrooms is not exhaustive, and the present method grows virtually any edible (or extract-edible) fungus with the improved profiles, speed and purity described herein.

Although the invention has been described in detail in the previous passages of this specification, the following examples are illustrative.

Example 1

A seed blend containing purple corn, black quinoa, red quinoa, red canihua, black chia, black cumin, red flax seed and purple rice was blended in the ratio of about 93% by weight purple corn with the remaining 7% by weight being equally distributed among the other seven seeds. The seed mix was moistened with −600 ORP water and incubated for germination for 36 hours prior to inoculation with *Cordyceps sinensis* mycelium starter. The substrate was irrigated with the same −600 ORP water throughout mushroom cultivation and from the time of inoculation to the time of mushroom harvest the room containing the mushroom culture contained no transmissions of light or sound other than music containing the tone frequencies of 396 Hz, 417 Hz, 444 Hz, 528 Hz, 639 Hz, 741 Hz and 852 Hz maintained at or below 60 decibels and visible light transmission of about 1000 lumens per 25,000 square feet of cultivation space in the color ranges "throughout the rainbow" but without yellow, namely, purple, blue, green, orange and red and shades in between. The *Cordyceps sinensis* grown with this protocol was initially expected to grow during a period of 21 days, but in fact matured in 13 days with concomitant antiproliferation of unwanted competing organisms (the benefit of which is commercially and nutritionally huge).

Example 2

The same mushroom culture method as described in Example 1 is carried out again, but this time the inoculated mycelium is *Ganoderma lucidum*, not *Cordyceps sinensis*, and the eight seed blend was replaced with a five seed blend containing purple corn, purple rice, red flax seed, red canihua and black black quinoa. About 65% by weight of the seed blend is purple corn and the remaining seeds are distributed evenly among the remaining 35% by weight distribution of the seed blend. Germination in advance of inoculation, and growth of the mycelium inoculum to finished mushrooms, continues according to Example 1.

Example 3

The same mushroom culture method as described in Examiner 1 is carried out again, but this time the inoculated mycelium is *Armillaria mellea* and the seed blend for the substrate contains 50% red flax seed, 25% black chin and 25% red canihua.

Although the invention has been described with particularity above, with reference to particular ingredients and method steps and other specifics, the invention is only to be limited insofar as is set forth in the accompanying claims.

The invention claimed is:

1. A method of improving the growth and constitution of edible mushrooms, comprising the steps of blending a seed-based growth substrate containing between 3 and 8 seeds selected from the group consisting of corn, quinoa, canihua, chia, cumin, flax seed and rice, moistening said seed blend with structured, energized water, germinating said seed-based growth substrate for between 18 and 48 hours prior to inoculating mycelium starter consisting of a culinary or medicinal mushroom mycelium starter on said growth substrate and growing the resulting mushrooms for 13-15 days in the presence of one or more of the sound frequencies selected from the group consisting of 396 Hz, 417 Hz, 444 Hz, 52.8 Hz, 639 Hz, 741 Hz and 852 Hz and also in the presence of transmission of colored light.

2. The method of claim 1, wherein said seed-based growth substrate contains one or more red, purple or black colored seeds.

3. The method of claim 1, wherein said seed-based growth substrate contains at least red canihua, red flax seed and black chia.

4. The method of claim 1, wherein said seed-based growth substrate contains at least three of purple corn, black quinoa, red quinoa, red canihua, black chia, black cumin, red flax seed, and purple rice.

5. The method of claim 1, where said seed-based growth substrate contains all of purple corn, black quinoa, red quinoa, red canihua, black chia, black cumin, red flax seed and purple rice.

6. The method of claim 1, wherein said sound frequencies are transmitted along with music containing tones corresponding to said frequencies and further wherein said music is transmitted at a level between 50-80 decibels.

7. The method of claim 1, wherein said colored light is present at a strength of between 250 to 3000 lumens per 25,000 square feet of mushroom culture space and includes the colors purple, blue, green, orange and red and shades in between (but not yellow).

8. The method of claim 1 wherein said structured, energized water is enhanced ORP water that has an ORP value between −400 and −600.

9. The method of claim 1, wherein said seed-based growth substrate contains purple corn, purple rice, red flax seed, red canihua and black quinoa, with about 65% of said seed-based growth substrate's being purple corn, and with the remaining 35% by weight being distributed evenly among said purple rice, said red flax seed, said red canihua and said black quinoa.

* * * * *